United States Patent [19]

Dabi et al.

[11] Patent Number: 4,933,390

[45] Date of Patent: Jun. 12, 1990

[54] IN SITU CROSSLINKING OF POLYELECTROLYTES

[76] Inventors: Shmuel Dabi, 218 N. 2nd Ave., Highland Park, N.J. 08904; Jayson C. Vassallo, 106 Cold Stream Ct., Emmaus, Pa. 18049

[21] Appl. No.: 86,017

[22] Filed: Aug. 17, 1987

Related U.S. Application Data

[63] Continuation-in-part of Ser. No. 749,907, Jun. 28, 1985, abandoned.

[51] Int. Cl.$^5$ ............................................. C08J 43/00
[52] U.S. Cl. ..................... 524/808; 428/283; 428/402; 428/913; 524/811; 524/813; 526/301; 526/302; 526/304; 526/307; 526/312; 526/321; 526/273
[58] Field of Search ............... 526/301, 304, 302, 307, 526/312, 321, 273; 428/913, 283, 402; 524/808, 811, 813

[56] References Cited

U.S. PATENT DOCUMENTS

| | | | |
|---|---|---|---|
| 4,059,556 | 11/1977 | Neukam | 526/208 |
| 4,076,922 | 2/1978 | Satoh et al. | 526/97 |
| 4,079,029 | 3/1978 | Gross | 128/156 |
| 4,100,143 | 7/1978 | Wolf et al. | 526/301 |
| 4,310,593 | 1/1982 | Gross | 428/290 |
| 4,718,899 | 1/1988 | Itoh et al. | 604/368 |

*Primary Examiner*—James J. Bell

[57] ABSTRACT

A composition, useful for forming absorbent articles of a carboxylic polyelectrolyte, is prepared by copolymerizing a carboxylic polyelectrolyte monomer, a reactive self-crosslinking monomer and a hydrophobic monomer. The composition in the form of an emulsion or a viscous solution has an extendable shelf life and may be used to produce a superabsorbent material or a substrate impregnated with a superabsorbent material.

32 Claims, No Drawings

IN SITU CROSSLINKING OF POLYELECTROLYTES

BACKGROUND OF THE INVENTION

This application is a continuation-in-part of application Ser. No. 749,907 filed June 28, 1985, now abandoned.

This invention relates to products for absorbing aqueous fluids and, in particular, products for absorbing body fluids. The invention is specifically directed toward compositions for producing crosslinked polyelectrolytes which compositions are usable in commercial products for absorbing aqueous liquids and are particularly useful in producing absorbent composite materials which are coated or impregnated with such compositions and subsequently treated so as to produce a composite material incorporating polyelectrolyte which is crosslinked in situ.

Highly absorbent crosslinked polyelectrolytes and methods for preparing the same are already known. U.S. Pat. Nos. 3,669,103 and 3,670,731 teach the use of these materials in diapers and dressings. U.S. Pat. Nos. 2,988,539; 3,393,168; 3,514,419 and 3,557,067 teach methods of making such absorbents and, in particular, are related to making water swellable crosslinked carboxylic copolymers that are either crosslinked during copolymerization or crosslinked after polymerization and then neutralized to result in pendant ionic moieties capable of imparting water retention properties to a finished material.

Further, the process of incorporating such polyelectrolytes or their monomeric precursors into a substrate such as a fibrous web or a cellular, i.e. foam, material and then crosslinking in situ, is also known. Published European Patent Office Application 81302086.4 discloses impregnating a fibrous web with a solution of monomers, with or without crosslinking agents and then irradiating such impregnated web to polymerizing and/or crosslink in situ. U.S. Pat. Nos. 4,076,673; 3,980,663; 4,071,650 all exemplify teachings of preparing solutions for coating substrates which subsequently may be treated to produce in situ crosslinked polyelectrolytes.

Unfortunately, these foregoing suggestions suffer from several drawbacks when it is contemplated to translate such suggestions into commercial processes. Suggestions directed toward irradiation techniques, when scaled to commercial proportions, require large capital investment for irradiating equipment such as, for example, an electron beam device, and, concommitantly, consume large quantities of energy for carrying out such processes. Additionally, in order to obtain high conversion of monomer to polymer, such irradiation technique requires still more energy input and also tend to over crosslink the polymer resulting in a decrease in absorption capacity.

Those suggestions relating to preparing compositions comprising polyelectrolytes and crosslinking agents and then applying such composition to a substrate are also fraught with problems on a commercial level. A major drawback to such systems is the limited shelf life of the impregnating or coating concentration. Almost immediately upon mixing the polyelectrolyte with the crosslinker, a reaction begins that leads to gel formation. Once gelled the composition can no longer be used. Accordingly, a commercial process must, to utilize such suggestions, apply the components i.e., the polyelectrolyte and the crosslinker, in separate steps and hence suffer the concommitant inconvenience as well as the likelihood of locally applied non-uniform proportions of these components. The problem is compounded when such commercial processes are designed to impregnate a substrate with excess composition and then recirculate to reuse the excess. Such a system will be encountered when attempts are made to impregnate a fibrous or cellular web with vacuum deposition techniques such as are common in the art of producing bonded non-woven fabrics. In such a process, of necessity, the active components are intermixed and gelling follows.

Accordingly, there is a need for providing a commercial process for in situ crosslinking of polyelectrolytes to make absorbents, and especially superabsorbents.

The most pertinent prior art reference, Gross, U.S Pat. No. 4,079,029, discloses one possible way of doing this, involving: a solution useful to form water swellable articles of a carboxylic synthetic polyelectrolyte upon curing which comprises 1. a solvent selected from the group consisting of water, lower alcohols and mixtures thereof,
2. about 5 to about 60% by weight based on (1), of a crosslinkable carboxylic copolymer which contains in the copolymer
    (A) about 25 to about 98% by weight based on the total weight of the copolymer of an alkali metal salt of an olefinically unsaturated monocarboxylic acid;
    (B) about 2 to about 50% by weight of an olefinically unsaturated monocarboxylic acid;
    (C) about 25 to about 60% by weight of an alkyl ester of an olefinically unsaturated monocarboxylic acid and
    (D) about 0.3 to about 5.0% by weight of crosslinking units of an N-substituted acrylamide or methacrylamide having the formula $H_2C=CR-C(O)-NHCH_2-O-R^1$ wherein R is selected from hydrogen or methyl and $R^1$ is hydrogen or an alkyl group of 1-8 carbons.

The Gross patent specifically listed the following as examples of the N-hydroxymethyl or N-alkoxymethylene acrylamides or methacrylamides usable there:
N-methoxymethyl acrylamide,
N-propoxymethyl acrylamide,
N-isopropoxymethyl acrylamide,
N-ethoxymethyl acrylamide,
N-methylol acrylamide,
N-butoxymethyl acrylamide, and
N-tertiary butoxy methyl acrylamide,
N-isobutoxymethyl acrylamide,
N-octyloxymethyl acrylamide,
N-methoxymethyl methacrylamide,
N-propoxymethyl methacrylamide,
N-isopropoxymethyl methacrylamide,
N-ethoxymethyl methacrylamide,
N-methylol methacrylamide,
N-butoxymethyl methacrylamide,
N-tertiary butoxy methyl methacrylamide,
N-isobutoxymethyl methacrylamide, and
N-octyloxymethyl methacrylamide.

In said Gross U.S. Pat. No. 4,079,029, the method of making water swellable films involves starting with the above composition of the polyelectrolytes having a pH range from 7 to 9 which subsequently is acidified by adding organic or inorganic acids to a pH range 3 to 6 and spread on a flat plate or roller of metal, plastic, or other impervious substrate and heated to a temperature greater than 30° C. to crosslink the polyelectrolyte and drive off the excess water and/or alcohol. The film is then peeled off the plate or roller by a scraper to recover the intact film for subsequent storage or use.

The present invention takes an opposite approach from said Gross patent, by starting with polyelectrolytes having an acid pH range and then increasing the pH (in contrast to Gross which starts with polyelectrolytes having a basic pH range and then decreasing the pH). The present invention uses a broader (but overlapping) reactive self crosslinking monomer than does Gross. It was defined in the parent application Ser. No. 749,907 of this application as one having the formula:

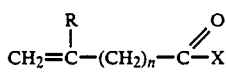

wherein R is H or CH$_3$, n is 0 or 1-5, and X is a group capable of reacting through self condensation or with carboxylic acid by condensation or ring opening, preferably wherein X is glycidyl, N-methylol, N-methylol alkyl ether having alkyl groups of 1-4 carbons, blocked isocyanate, N-methylol urethane, or aziridine.

Of the above possible definitions of X, said Gross patent discloses X=N-methylol and X=N-methyol alkyl ether having alkyl groups of 1-4 carbons, and thus overlapped to that extent only. [The overlap is omitted from the claims of this CIP application]

The Gross patent calls for a polyelectrolyte involving a copolymer having 4 different monomeric units, designated above as 2A., B., C. and D. Applicant's comparable polyelectrolyte at first appears different by involving a copolymer having only 3 different monomers, by lacking monomeric unit 2B which Gross defines as "about 2 to about 50% of an olefinically unsaturated monocarboxylic acid". However, under certain pH conditions (e.g. at pH5) Applicant's monomer comparable to Gross' monomeric unit 2A . . . "an alkali metal salt of an olefinically unsaturated monocarboxylic acid" exists in equilibrium with the free acid, so that some of Applicant's polyelectrolytes overlap with those of Gross under certain limited conditions.

The presence of free carboxylic acid is a function of the pH of the polymer solution. At pH=5 about 50% of a polyacrylic acid polymer is in the acidic form. However, by increasing the pH to 9 all of the acid groups are converted to the carboxylate salt. The crosslinking reaction, described in Gross U.S. Pat. No. 4,079,029 will not take place unless the pH is reduced to below pH=6. This is described in column 3 lines 27-28, and is reflected in the Gross Patent Claim 2B as a free carboxylic acid, 2% to 50% by weight.

In the present invention, in contrast to Gross, the best mode of making the superabsorbent involves increasing the pH to 9 with ammonium hydroxide solution, followed by drying and crosslinking. If this is done with sodium hydroxide, no crosslinking takes place (as demonstrated in Example II below) and no superabsorbent is formed. Additionally, a significantly more absorbent polymer is made from the pH=9 solution as compared to the pH=5 (see examples I, II below). Thus, a key difference between this invention of this application and Gross U.S. Pat. No. 4,079,029, is, that here the solution, from which an absorbent polymer is prepared, should have a pH greater than 7, preferably 9, and that at least 50% (by mole) of the neutralizing base must be ammonium hydroxide. The alkaline pH also increases the shelf life of the solution in the present invention.

SUMMARY OF THE INVENTION

In accordance with the teachings of this invention a composition and process is provided that can be employed for coating or impregnating a substrate, which will deposit polyelectrolyte onto or into the substrate and which polyelectrolyte can be crosslinked by subsequent drying or heating in situ. The composition is so selected as to have a long shelf life and will not gel prior to use or after it is collected as a reusable, recirculated composition.

Specifically, the invention contemplates utilizing, with modification, a technique employed in the art of manufacturing acrylic fibers such as are produced from spinnable solutions of copolymers comprising acrylonitrile. In U.S. Pat. Nos. 4,059,556 and 4,100,143; for example, it is taught that non-poly(electrolytic) acrylonitrile copolymers may be provided which are self cross-linking by the inclusion therein of a comonomer which is capable of crosslinking upon drying or heating. Such comonomers suggested are exemplified by N-methyl alkyl ether acrylamides and N-methylol compounds or N-methyl ethers of unsaturated mono- or bis-urethanes. As is taught in the art of fiber production exemplified by these patents, emulsions of such self crosslinking copolymers are employed and may be stabilized by either incorporating additives into the emulsion e.g. mineral salts, α-amino carboxylic acids or by effecting the copolymerization reaction in strongly polar organic solvents such as dimethyl formamide or dimethyl sulphoxide. It is also mentioned in these references that additional optional monomers may be copolymerized into the polymer, such optional monomer having been conventionally employed in the acrylonitrile fiber technology and exemplified by such monomers as acrylic acid and methacrylic acid alkyl esters, among others. The purpose of these monomers, as has been employed in the acrylonitrile fiber technology is to render the copolymer crosslinkable.

It has now been discovered that a composition, useful for forming absorbent articles comprising crosslinked carboxylic poly(electrolyte) may be provided by employing an emulsion of the poly(electrolyte) copolymerized with monomers of the kind that produce self crosslinking copolymers, as employed in the acrylic fiber art. Moreover, it has been discovered that the problem of emulsion instability is cured in the case of self crosslinking poly(electrolyte) copolymers without resorting to undesirable additions or to employing, for the dispersing phase of the emulsion, organic solvents.

Indeed, it has been discovered that when attempting to utilize the teachings of the acrylic fibrous art, in the use of polyelectrolytes, a self crosslinkable copolymer cannot be conveniently prepared. The presence of the acidic groups in the electrolyte monomers tends bringing about premature gelling, i.e. crosslinking, during the copolymerization reaction and renders the composition useless for the purposes of this invention.

It has now been discovered that the techniques of producing self crosslinkable copolymers may be applied to the art of in situ crosslinking of polyelectrolytes, provided that, in addition to the polyelectrolytes and reactive self crosslinking monomers, the copolymer also includes an effective proportion of hydrophobic comonomers.

Specifically, it has been discovered that a composition, useful for forming absorbent articles of a carboxylic polyelectrolyte may be prepared which composition comprise a polymer which is copolymerized from:

(a) a carboxylic polyelectrolyte monomer;
(b) a reactive self crosslinking monomer having the formula:

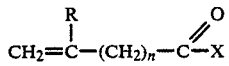

wherein R is selected from the groups consisting of H or CH$_3$, n is selected from the group consisting of zero or the integers 1 to 5, and X is selected to be a group capable of reacting through self condensation or with carboxylic acid by condensation or ring opening; and (c) a hydrophobic monomer.

As used herein, hydrophobic monomer is meant to define a water immiscible monomer which, when present in sufficient quantity, will maintain the un-neutralized acidic polymer resulting from the above composition in the emulsion state. The hydrophobic monomer preferably is selected as an alkyl ester of acrylic or methacrylic acid, said alkyl group having from one to eight carbon atoms, and preferably from one to four carbon atoms. Preferably, the reactive self crosslinking monomer, (b), is one in which X is selected from the group consisting of glycidyl, N-methylol, N-methylol alkyl ether having alkyl groups of from one to four carbon atoms, blocked isocyanate, N-methylol urethane, or aziridine. To avoid overlap with Gross U.S. Pat. No. 4,079,029, whenever X is N-methylol or N-methylol ether, the pH of the polyelectrolyte is above pH7. When X has any of its other possible definitions, the pH is immaterial, although best results are obtained at pH 7 or above.

In many cases, depending upon the reactivity of the crosslinkable monomer selected, the emulsion resulting from the copolymerization reaction, of the above-described composition is stable and will not crosslink after a substantial period of time. In some cases, however, it is preferred, soon after forming such emulsion, to neutralize the composition to a pH of greater than 5 by employing, for example, an aqueous sodium hydroxide solution. This neutralization renders the copolymer soluble, breaks the emulsion, and has been found to substantially increase the shelf life of the resulting solution without affecting its ability to self crosslink upon drying and/or heating.

The best results, in terms of the highest absorbency of the final product, are obtained by neutralizing and alkalinizing the composition to a pH above 7, and preferably to pH9, using ammonium hydroxide for this purpose. If the neutralizing base used is NaOH, a soluble product is obtained instead of a swellable one. But, when the neutralizing base used contains at least 50% (mole %) of ammonium hydroxide, a swellable superabsorbent is obtained.

The solution is employed by coating or impregnating various substrates and then drying and/or heating to result in in situ crosslinked absorbent polymer.

DETAILED DESCRIPTION OF THE INVENTION

The invention concerns self crosslinking polyelectrolyte copolymers of polyelectrolyte moieties, self crosslinking reactive moieties and hydrophobic moieties.

The carboxylic polyelectrolyte moieties capable of being crosslinked in accordance with the teachings of this invention are well known and are described in detail in U.S. Pat. No. 4,310,593 which is incorporated herein by reference. The essence of usable polyelectrolytes is that they comprise, at least in the salt form, sufficient carboxylate groups to render them water soluble. Usable polymers, capable of being prepared from readily available monomers and converted into their salt form include, for example, acrylic acid-acrylate copolymers; acrylic acid-acrylamide copolymers; acrylic acid-olefin copolymers; poly acrylic acid; acrylic acid-vinyl aromatic copolymers; acrylic acid-styrene sulfonic acid copolymers; acrylic acid-vinyl ether copolymers; acrylic acid vinyl acetate copolymers; acrylic acid-vinyl alcohol copolymers; copolymers of methacrylic acid with all of the above comonomers; copolymers of maleic acid, fumaric acid and their esters with all of the above comonomers; copolymers of maleic anhydride with all of the above comonomers.

The self crosslinking reactive moieties are provided by copolymerizing together with the polyelectrolyte, reactive groups having the formula:

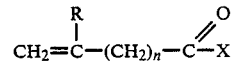

wherein R is selected from the group consisting of H or CH$_3$, n is selected from the group consisting of zero or the integers 1 to 5, and X is chosen to be a group capable of reacting either through self condensation or, with carboxylic acid, through condensation or a ring opening mechanism.

Thus, for example, X may be selected from the group consisting of glycidyl; N-methylol; N-methylol alkyl ether wherein the alkyl group has from 1 to 4 carbon atoms; blocked isocyanates such as, for example, an isocyanatoethyl methacrylate - caprolactam adduct, N-methylol urethane; aziridine or the like.

To differentiate from, and avoid inadvertant overlap with compositions of Gross U.S. Pat. No. 4,079,029, when X is N-methylol or N-methylol alkyl ether, the pH of the solution must be above pH 7. For the other definitions of X, the pH can be either above or below pH7.

Reactive groups such as are described above have already been incorporated in copolymers to produce self crosslinking polymers (see for example U.S. Pat. Nos. 4,100,143 and 4,059,556). However, such self crosslinking polymers as have employed these groups are primarily hydrophobic in nature. The present invention, instead, involves self crosslinking copolymers wherein the carboxylic groups (acids and salts thereof) represent a substantial portion of the copolymer and specifically range from 20% to 82% of the copolymer, on a weight basis and preferably from 35 to 75 percent, by weight.

The presence of this high proportion of carboxylic groups, while necessary to result in a polyelectrolyte having a high capacity for absorbing aqueous fluids, has a concomitant disadvantage, when copolymerized with the reactive, self crosslinking groups as set out above. It has been discovered that almost immediately after the copolymer reaction is carried out, because of the presence of this high proportion of carboxylic groups, the crosslinking reaction, being catalyzed by acid, begins. The result is that the copolymerized composition quickly turns to gel. For example, a copolymerization reaction of meth(acrylic) acids with 1 to 2%, by weight, glycidyl methacrylate or with N-methylol acrylamide, carried out in water at 70° C., turned into a gel in about twenty minutes. Clearly such composition is not conveniently usable for the purposes described herein.

In accordance with the teachings herein, it has been discovered that this problem may be greatly ameliorated by copolymerizing a third moiety group into the self cross-linking polymer. Generally, said third moiety is a hydrophobic monomer i.e., a water immiscible monomer. The hydrophobic monomer is copolymerized into the self crosslinking polyelectrolyte chain in sufficient quantity to preclude premature gelation. While such quantity may vary with such features as the specific moieties chosen for all three types of copolymers, generally such quantity should represent about 5 to about 70% by weight of the finished poly(electrolyte) self crosslinking copolymer. Preferably such range should be from about 10 to about 35%. Suitable hydrophobic comonomer may be selected from the group consisting of the alkyl esters of acrylic and methacrylic acid wherein said alkyl groups consist of from one to four carbon atoms.

It has been discovered that by incorporating such above-described hydrophobic groups into the polyelectrolyte self crosslinking copolymer, the resulting composition has a significantly greater shelf life wherein the tendency to prematurely crosslink and gel is greatly reduced. Without being bound to any particular theory, it is believed that the primary function of these hydrophobic moieties is to maintain the reaction product of the copolymerization process in the dispersed phase of an aqueous continuous phase emulsion when the reaction is completed. In the emulsion form, the copolymers produced are coiled, with a preponderance of the crosslinkable groups hidden inside the colloidal particles and, hence, less accessible for the crosslinking reaction.

The retardation of the crosslinking reaction is effective in all cases by incorporating the hydrophobic moiety. Still greater retardation may be achieved by employing the teachings of this invention with further modification. Since crosslinking is retarded, there is now sufficient time to complete the copolymerization reaction and then further treat the reaction mixture by neutralizing the acid functions to a pH of 5 or greater. The emulsion is broken by such neutralization and a clear viscous solution results. This neutralized solution has been found to have exceptionally long shelf life and is preferred when such long life is a consideration. Needless to say, it is important to first copolymerize the copolymers of polyelectrolyte and self crosslinking moieties with the hydrophobic polymeric moieties, as taught above, in order to have sufficient time to carry out the subsequent neutralization reaction without encountering premature gelation.

The neutralization step is most preferably used when employing as the self crosslinking moieties, a particularly reactive type, such as for example a glycidyl moiety.

The highest absorbency is found in products made by neutralizing the acid functions to a pH above 7, preferably 9, by using ammonium hydroxide.

Preferably, the reaction is carried out in water. The reaction may be carried out at pressures ranging from subatmospheric to super atmospheric pressure and at temperatures of from 15° C. to reflux, and may be catalyzed by such free radial generating compounds such as peroxide or azo compounds. Preferably the reaction is accomplished by using an oxidation/reduction initiator such as, for example, persulfate, bisulfite and ferrous ions. When this latter method is employed, a relatively low polymerization temperature will be sufficient to carry out the reaction. Low temperatures will also aid in the retardation of premature gelation.

The composition of this invention is useful for producing a wide variety of product and material having the common property of absorbing large quantities of aqueous liquids. For example, one employment of the composition is to produce a powdery "superabsorbent", i.e. an absorbent material capable of absorbing at least ten times its own weight of aqueous liquid. Such powder may be obtained by the mere heating and/or drying of the composition, prepared in accordance with the teachings of this invention either in the form of an emulsion or neutralized solution. The composition is cast upon a substrate to form a crosslinked polyelectrolyte film which is subsequently crushed into a powder. It should be noted, of course, that the film itself has substantial absorbent properties and is useful in some applications directly without the need for crushing into a powder.

The composition of this invention, when employed in the manner indicated above to produce a powder or film, manifests certain unique advantages. Typically, prior synthesis of superabsorbent materials involved the steps of synthesizing the polymer in question in an aqueous medium and then drying the reaction mixture to provide a dry superabsorbent powder. Such prior process are described, for example, in U.S. Pat. Nos. 4,090,013 and 4,320,040. The drawback in such a system is that the superabsorbent is formed in the presence of large quantities of water and, owing to the highly absorbent properties of the polymer, a great quantity of water will be tightly bound to the polymer. Accordingly, drying to a powder, for example, is exceedingly difficult and involves a high energy input. On the other hand, the obvious alternative is to use an organic solvent. Unfortunately the drawback is high cost, high volatility and the danger of explosion.

In another embodiment of this invention, the composition made in accordance with the teachings herein is employed to enhance the aqueous liquid absorption characteristics of an aqueous liquid impregnable substrates. Such substrates may comprise, for example, fibrous webs of cellulosic or synthetic fiber, either woven or non-woven, or loosely associated batts of such fibrous material. Additionally, such substrates may comprise cellular polymeric material, i.e. foams such as for example, polyurethane foam or regenerated cellulose foam. In such embodiment the composition of this invention is sprayed, padded, flooded or otherwise applied to the substrate and preferably impregnated into the substrate by means well known in the art such as applying a differential pressure by mechanical compression or vacuum application. The application of the composition to the web may be selective, i.e. not uniform over the entire surface of the web but instead in a pattern such as a grid pattern, elongated stripes of a desired width, spots, or the like. Additionally, the depth of penetration into the Z-direction of the web may be controlled by, for example, appropriate control of the vacuum applied, where vacuum deposition is the selected deposition method. The impregnated web is then dried and/or heated, and the deposited copolymer crosslinks, in situ, to provide a substrate of enhanced absorbency.

It will be apparent to one skilled in the art that the production of substrates incorporating deposited superabsorbent material are made commercially in large volume, generally by treating a continuously moving web of substrate material. It will also then be apparent that the unique long shelf life of the composition of this invention is particularly advantageous to such production. Further, the composition of this invention will greatly facilitate the drying of the impregnated substrate. Prior methods involving in situ polymerizing and/or crosslinking of deposited material on a substrate have been based on processes whereby the polymerization and/or crosslinking occurs while substantial quantities of the dispersing phase, generally water, is still present. Accordingly the final polymer is a superabsorbent material which will, because of the presence of large quantities of water, absorb and retain such water aggressively. Therefore, drying of the substrate has also been difficult. In contrast therewith, by employing the composition of this invention, the self crosslinking does not actually occur until a great preponderance of the water present in the composition has been first removed. It is only at this point that the copolymer becomes a superabsorbent and, hence, less of a quantity of tightly held water need be removed by following the teachings of this invention.

The products described above, e.g. the super absorbent powder, film and substrates are useful in the manufacture of various products having in common the property of employment for absorbing liquids in general, and for absorbing body fluids in particular. Typically, the products of this invention may be used as the absorbent element or as one of several absorbent elements in products such as sanitary napkins, catamenial tampons, incontinence pads, underpads for beds and the like, dressings, clothing shields such as panty liners or underarm dress shields, wound dressings, disposable diapers and similar products.

In order to better understand the teachings of this invention, the following examples are given:

COMPARATIVE EXAMPLE 1

Seven hundred and fifty mls. of distilled water are charged into a one liter flask which is equipped with agitation equipment, a nitrogen purge source and a thermocouple. The liquid is de-airated for a half hour with nitrogen to dispel any dissolved oxygen which might otherwise inhibit the copolymerization reaction. During this time, the water is heated to 70° C. After reaching this temperature, 0.5 g of potassium/sulfate are dissolved in 20 mls. of distilled water and added to the reaction vessel. Within one minute 80 mls. of acrylic acid, having a purity of 99% by weight and 20 mls. of methacrylic acid having a minimum purity of 98% by weight, are added to the reaction vessel. Immediately following the addition of these monomers, 1 ml. of glycidyl methacrylate, the reactive crosslinkable monomer, is added to the reaction vessel. The reaction is allowed to proceed for 30 minutes. At this point, it is noted that the reaction mixture has crosslinked and formed an unworkable gelled material.

COMPARATIVE EXAMPLE 2

The procedure of Example 1 is repeated with the exception that in lieu of the 1 ml. of glycidyl methacrylate as the reactive crosslinkable monomer, 2 mls. of a 60% aqueous solution of N-methylol acrylamide is employed. Again, after heating the reactants for 30 minutes, it is noted that the reaction mixture has crosslinked and an unworkable gelled material results.

As can be seen from the above examples, the copolymer obtained and comprising polyelectrolyte in combination with self crosslinking reactive monomers is not usable in the processes of this invention because of premature gelling.

EXAMPLE 1

Seven hundred and fifty mls. of distilled water are charged into a one liter flask equipped with agitation means and nitrogen purge means and thermocouple. The liquid is de-airated for one half hour with nitrogen while simultaneously being heated to 70° C. After reaching the desired temperature, the nitrogen purge is removed and positioned over the surface of the solution to maintain a nitrogen blanket. Thereafter, 15 gms. of a 30% by weight aqueous solution of sodium laurel sulfate, a surfactant, are added to the solution together with 0.5 gm. of potassium/sulfate dissolved in a solution of 20 mls. of distilled water. Within one minute, 85 mls. of acrylic acid and 15 mls. of the hydrophobic monomer methyl methacrylate, having a minimum purity of 98% by weight are added to the reaction vessel. Following the addition of these monomers, 1 ml. of glycidyl methyl methacrylate is added to the reaction vessel and the reaction is allowed to proceed for 30 minutes. The reaction mixture resulting from this procedure is a stable, fluid, milky white emulsion. Half of this emulsion is allowed to stand at room temperature, and it is only after two days that it is noted that a small portion of the emulsion has undergone crosslinking and gelled. The second half of the emulsion obtained from the reaction is treated with a 50% by weight aqueous sodium hydroxide solution in sufficient quantity to raise the pH to about 5. Upon the addition of the sodium hydroxide solution a viscous clear solution results. This neutralized solution is also allowed to stand at room temperature, and after two days appears to be fluid, workable and non-gelled.

The neutralized solution is dried for 15 minutes at 120° C. and a film is obtained. The film is crushed to result in superabsorbent powder. The powder is tested for absorbency using the free absorbency method which comprises placing 0.1 grams of the powder in a beaker containing 15 mls. of a 1% by weight sodium chloride aqueous solution. The dispersed superabsorbent in the sodium chloride solution is filtered, excess water is allowed to drain by gravity, and the remaining material is weighed. It is determined that the powder has absorbed 40 gms of the solution per gram of dried powder.

EXAMPLE 2

(A comparative example which overlaps Gross U.S. Pat. No. 4,079,029)

Again, as in Example 1, 750 mls. of distilled water are charged to the 1 liter flask, the liquid is de-airated with nitrogen and heated to 70° C. The surfactant and potassium per sulfate are added and then, within one minute, 70 mls. of acrylic acid, 20 mls. of methacrylic acid and, as the hydrophobic monomer, 10 mls. of N-butyl acrylate are added. Immediately following the addition of these monomers, 2 mls. of a 60% aqueous N-methylol acrylamide, a less reactive crosslinking monomer than the glycidyl methacrylate recited in Example 1, is added. The reactants are heated for 30 minutes and a stable, fluid, milky white emulsion is obtained. Half the emulsion is neutralized with enough 50% by weight sodium hydroxide aqueous solution to result in a clear solution having a pH of 5. The other half remains in the emulsion form. Both portions are stored for one month at room temperature, and it is observed that in this case, employing the less reactive self crosslinking monomer, both the emulsion form and the neutralized form are still fluid, workable polymer solutions. The solutions are capable of being employed in each of the processes set out above to produce highly absorbent material.

EXAMPLE 3

The neutralized solution obtained from the procedures of Example 1 is utilized to construct an absorbent structure by applying it to a polyester fibrous web. A carded polyester fibrous web having fibers of a denier of 8.5, staple fiber length of 1.5 inches, and a basis weight of 1 oz/yd$^2$, is saturated with the solution and excess is removed by vacuum suction. The web is then dried for 20 minutes at 120° C. resulting in a structure consisting of 40% by weight of the polyester fibers and 60% by weight of in situ crosslinked polymer. A sample of this material is tested for maximum capacity and fluid retention utilizing a mechanized form of the porous plate Testing apparatus as described in detail in Textile Research Journal 37, pp. 356–366, 1967. Briefly, this test involves placing the sample in what is essentially a Buchner funnel having a porous bottom plate and holding the sample in place by applying thereon a standard weight to maintain a standardized confining pressure. In the case of this test, the confining pressure was 0.07 psig. The porous plate is placed in contact with a reservoir of fluid which again for this test comprises a 1% by weight sodium chloride aqueous solution, and the sample is allowed to absorb the fluid through the porous plate until saturated. By maintaining the sample at 1.5 cm above the level of the reservoir to avoid flooding, the fluid absorbed is subjected to essentially zero hydrostatic head with respect to the reservoir. The volume of fluid absorbed, divided by the weight of the sample, is termed the maximum capacity. To determine fluid retention, the saturated sample is elevated with respect to the reservoir thereby imposing a hydrostatic head upon the fluid absorbed, the head arbitrarily being chosen as 35 cm of fluid. The apparatus is provided with means for measuring the volume of fluid retained under the hydraulic head. Retention values are reported as the volume retained per unit weight of the sample. The results of this test for the web of this example resulted in a maximum capacity of 18 ml/gram of 1% aqueous sodium chloride and a retention value of 11 ml/gram.

EXAMPLE 4

Five hundred and seventy-five mls of distilled water were charged into a one liter flask equipped with agitation and nitrogen purge means and thermocouple. The liquid was deaerated for one half hour with nitrogen while simultaneously being heated to 35° C. After reaching the desired temperature, the nitrogen purge was removed and positioned over the surface of the solution to maintain a nitrogen blanket.

Thereafter, 20 gms of a 30% by weight aqueous solution of sodium lauryl sulfate, a surfactant, were added to the solution. Then 0.75g of potassium persulfate and 0.75g of sodium metabisulfite were added along with 6 ml of 0.15% ferrous sulfate solution. Within one minute, 144g of acrylic acid and 53 mls of the hydrophobic monomer methyl methacrylate, having a minimum purity of 98% by weight were added to the reaction vessel. Following the addition of these monomers, 6 ml of 60% aqueous N-methylol acrylamide were added to the reaction vessel and the reaction was allowed to proceed for 3 hours, while the temperature was kept at 45° C. to 50° C. The resulting emulsion was treated with 72g of 50% sodium hydroxide solution to give a clear viscous solution with pH=5.5. The solution was cast into a 20 mil film and cured at 145° C. for 20 minutes. The dry film was ground to give superabsorbent particles (20 mesh in size). The absorbency of this powder was measured as described in Example 1 above, and results are presented in Table I below compared with other powders.

EXAMPLE 5

The emulsion described in Example 4 was prepared again. Then a portion of that emulsion was neutralized with sodium hydroxide to pH=9 and another portion was neutralized to pH=9 with ammonium hydroxide. A powder was then prepared from each of the above resultant solutions as described in Example 4. The absorbency results are shown in Table I.

TABLE I

| Effect of pH and Neutralizing Agent on Absorbency | | |
|---|---|---|
| Sample | Solution pH | Absorbency g/g |
| Example 4 - Ammonia | 5.5 | 35 |
| Example 4 - Sodium Hydroxide | 5.5 | 36 |
| Example 5 - Ammonia | 9 | 56 |
| Example 5 - Sodium Hydroxide | 9 | 0 -Soluble |

It is clear from the above Examples 4 and 5 that the pH must be kept between 3–6 when neutralizing with sodium hydroxide (which is in accord with the teaching of U.S. Pat. No. 4,079,029). In the present invention, it is advantageous to raise the pH to 9 where a significantly higher absorbency is obtained, as well as a more stable solution. However ammonium hydroxide should be at least 50% of the neutralizing base, in order to obtain this most preferred result.

What is claimed:

1. A composition, useful for forming absorbent articles employing a carboxylic polyelectrolyte, comprising a poly(electrolyte) self crosslinking copolymer copolymerized from:
   (a) a carboxylic polyelectrolyte monomer;
   (b) a reactive self crosslinking monomer having the formula:

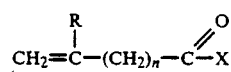

wherein R is selected from the group consisting of H or CH$_3$, n is selected from the group consisting of zero or the integers 1 to 5, and X is selected to be a group capable of reacting through self condensation or with carboxylic acid by condensation or ring opening; and
   (c) a hydrophobic monomer; wherein, whenever X in (b) above is either N-methylol or an N-methylol alkyl ether, the composition has a pH of at least 7.

2. The composition of claim 1, wherein the reactive self crosslinking monomer (b) is one in which X is selected from the group consisting of glycidyl, N-methylol, N-methylol alkyl ether having alkyl groups of from one to four carbon atoms, blocked isocyanate, N-methylol urethane or aziridine.

3. The composition of claim 1, wherein the hydrophobic monomer (c) is selected from the group consisting of alkyl esters of acrylic or methacrylic acid wherein said alkyl groups have from one to eight carbon atoms.

4. The composition of claim 3, wherein said alkyl groups have from one to four carbon atoms.

5. The composition of claim 1, wherein said hydrophobic monomer is present in sufficient quantity to result in 5 to about 70 percent by weight of hydrophobic monomer in said copolymer.

6. The composition of claim 5, wherein said hydrophobic monomer is present in sufficient quantity to result in 10 to 35 percent by weight of hydrophobic monomer in said copolymer.

7. The composition of claim 1, wherein said poly(electrolyte) monomer (a) is present in sufficient quantity to result in a copolymer containing about 20 to about 82 percent by weight of carboxylic groups.

8. The composition of claim 7, wherein said poly(electrolyte) monomer (a) is present in sufficient quantity to result in a copolymer containing about 35 to about 75 percent by weight of carboxylic groups.

9. The composition of claim 1 in the form of an emulsion wherein said copolymer is in the dispersed phase.

10. The composition of claim 1 in the form, of a viscous solution having a pH of at least 5.

11. The composition of claim 1 in the form of a solution having a pH of 9, wherein ammonium hydroxide was used to raise the pH.

12. An absorbent material made from the composition of claim 1.

13. The absorbent material of claim 12, wherein the reactive self crosslinking monomer (b) is one in which X is selected from the group consisting of glycidyl, N-methylol, N-methylol alkyl ether having alkyl groups of from one to four carbon atoms, blocked isocyanate, N-methylol urethane or aziridine.

14. The absorbent material of claim 12, wherein the hydrophobic monomer (c) is selected from the group consisting of alkyl esters of acrylic or methacrylic acid wherein said alkyl groups have from one to eight carbon atoms.

15. The absorbent material of claim 14, wherein said alkyl groups have from one to four carbon atoms.

16. The absorbent material of claim 12, wherein said hydrophobic monomer is present in sufficient quantity to result in 5 to about 70 percent by weiqht of hydrophobic monomer in said copolymer.

17. The absorbent material of claim 16, wherein said hydrophobic monomer is present in sufficient quantity to result in 10 to 35 percent by weight of hydrophobic monomer in said copolymer.

18. The absorbent material of claim 12, wherein said poly(electrolyte) monomer (a) is present in sufficient quantity to result in a copolymer containing about 20 to about 82 percent by weight of carboxylic groups.

19. The absorbent material of claim 16, wherein said poly(electrolyte) monomer (a) is present in sufficient quantity to result in a copolymer containing about 35 to about 75 percent by weight of carboxylic groups.

20. The absorbent material of claim 11 in the form of a powder.

21. The absorbent material of claim 11 in the form of a film.

22. A process for producing absorbent materials comprising:
(a) a carboxylic polyelectrolyte monomer;
(b) a reactive self crosslinking monomer having the formula:

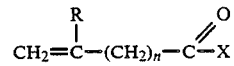

wherein R is selected from the groups consisting of H or $CH_3$, n is selected from the group consisting of zero or the integers 1 to 5, and X is selected to be a group capable of reacting through self condensation or with carboxylic acid by condensation or ring opening; and
(c) a hydrophobic monomer; wherein whenever X in (b) above is either N-methylol or an N-methylol alkyl ether, the composition has a pH of at least 7; copolymerizing said monomers to form a poly(electrolyte) self crosslinking copolymer dispersed in water; and drying said dispersion to produce absorbent material comprising crosslinked poly(electrolyte) copolymers.

23. The process of claim 22, wherein the reactive self crosslinking monomer, (b), is one in which X is selected from the group consisting of glycidyl, N-methylol, N-methylol alkyl ether having alkyl groups of from one to four carbon atoms, blocked isocyanate, N-methylol urethane, or aziridine; and wherein the pH of the poly(electrolyte) dispersion has its pH raised to 9 with ammonium hydroxide, whenever in (b) X is N-methylol or an N-methylol alkyl ether.

24. The process of claim 22, wherein the hydrophobic monomer (c) is selected from the group consisting of alkyl esters of acrylic or methacrylic acid wherein said alkyl groups have from one to eight carbon atoms.

25. The process of claim 24, wherein said alkyl groups have from one to four carbon atoms.

26. The process of claim 22, wherein said hydrophobic monomer is present in sufficient quantity to result in 5 to about 70 percent by weight of hydrophobic monomer in said poly(electrolyte) self crosslinking copolymer.

27. The process of claim 26, wherein said hydrophobic monomer is present in sufficient quantity to result in 10 to 35 percent by weight of hydrophobic monomer in said copolymer.

28. The process of claim 22, wherein said poly(electrolyte) monomer (a) is present in sufficient quantity to result in a copolymer containing about 20 to about 82 percent by weight of carboxylic groups.

29. The process of claim 28, wherein said poly(electrolyte) monomer (a) is present in sufficient quantity to result in a copolymer containing about 35 to about 75 percent by weight of carboxylic groups.

30. The process of claim 22, wherein the copolymerization is catalyzed by free radical generating compounds.

31. The process of claim 22, wherein the copolymerization is initiated by oxidation/reduction initiators selected from the group consisting of persulfate, bisulfite and ferrous ions.

32. The process of claim 21, wherein the shelf life of the dispersion is extended by neutralizing the dispersion to a pH of about 5 or greater, but to a pH of 9 using ammonium hydroxide whenever X in (b) is N-methylol or an N-methylol alkyl ether.

* * * * *